United States Patent

St. Germain et al.

Patent Number: 5,813,996
Date of Patent: Sep. 29, 1998

[54] GUIDE WIRE EXTENSION SYSTEM WITH MAGNETIC COUPLING

[75] Inventors: Jon P. St. Germain, Elk River; David J. Blaeser, Champlin; Roger N. Hastings, Maple Grove, all of Minn.

[73] Assignee: Scimed Life Systems, Inc., Maple Grove, Minn.

[21] Appl. No.: 576,601

[22] Filed: Dec. 21, 1995

[51] Int. Cl.⁶ .................................................... A61B 5/00
[52] U.S. Cl. ........................... 600/585; 600/434; 604/95; 604/280
[58] Field of Search .................................. 128/772, 657, 128/658; 604/95, 96, 280, 281, 282

[56] References Cited

U.S. PATENT DOCUMENTS

| Re. 34,466 | 12/1993 | Taylor et al. |
|---|---|---|
| 3,674,014 | 7/1972 | Tillander |
| 4,771,500 | 9/1988 | Kovacs |
| 4,827,941 | 5/1989 | Taylor et al. |
| 4,846,193 | 7/1989 | Tremulis et al. |
| 4,875,489 | 10/1989 | Messner et al. |
| 4,917,103 | 4/1990 | Gambale et al. |
| 4,922,923 | 5/1990 | Gambale et al. |
| 4,966,163 | 10/1990 | Kraus et al. |
| 5,031,636 | 7/1991 | Gambale et al. |
| 5,037,391 | 8/1991 | Hammerslag et al. |
| 5,047,045 | 9/1991 | Arney et al. |
| 5,109,867 | 5/1992 | Twyford, Jr. |
| 5,113,872 | 5/1992 | Jahrmarkt et al. |
| 5,117,838 | 6/1992 | Palmer et al. |
| 5,156,594 | 10/1992 | Keith |
| 5,188,621 | 2/1993 | Samson |
| 5,234,002 | 8/1993 | Chan |
| 5,269,759 | 12/1993 | Hernandez et al. |
| 5,404,888 | 4/1995 | Kontos et al. |
| 5,415,178 | 5/1995 | Hsi et al. |
| 5,441,055 | 8/1995 | Ales et al. |
| 5,464,023 | 11/1995 | Viera |
| 5,624,430 | 4/1997 | Eton et al. |

FOREIGN PATENT DOCUMENTS

WO 95/10976    4/1995    WIPO.

OTHER PUBLICATIONS

4–pg. Brochure entitled "The MAGNET Device", © Copyright1993, SCIMED Life Systems, Inc.

*Primary Examiner*—Max Hindenburg
*Assistant Examiner*—Pamela L. Wingood
*Attorney, Agent, or Firm*—Robert E. Atkinson

[57] ABSTRACT

A guide wire extension system is disclosed which utilizes a magnetic coupling to connect a guide wire to an extension wire. The magnetic coupling may include a magnetic portion and a magnetically responsive portion. Alternatively, the magnetic coupling may include a first magnet portion and a second magnet portion. The magnetic portions may be arranged coaxially or end-to-end. The magnetic portions may also be articulated. The magnetic coupling of the present invention provides an extension system which is both durable and relatively easy to use.

17 Claims, 4 Drawing Sheets

GUIDE WIRE EXTENSION SYSTEM WITH MAGNETIC COUPLING

FIELD OF THE INVENTION

The present invention generally relates to extendible guide members used to facilitate the advancement of medical devices. More specifically, the present invention relates to intravascular guide wire extension systems for use in combination with other intravascular devices such as balloon catheters. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well known in the art and typically involve the use of a balloon catheter with a guide wire, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

There are two basic types of balloon catheters used in combination with a guide wire, namely, over-the-wire (OTW) catheters and single operator exchange (SOE) catheters. The construction and use of both OTW catheters and SOE catheters are well-known in the art. An example of an OTW catheter may be found in commonly-assigned U.S. Pat. No. 5,047,045 to Arney et al. An example of an SOE balloon catheter is disclosed in commonly-assigned U.S. Pat. No. 5,156,594 to Keith.

During a typical intravascular procedure, it often becomes necessary to change intravascular devices. For example, in a PTCA procedure, it may become necessary to exchange a first balloon catheter having a relatively small balloon for a second balloon catheter having a relatively large balloon. To facilitate such an exchange using conventional SOE balloon catheter, no extension system is required. However, to facilitate such an exchange using a conventional OTW balloon catheter, it is necessary to make use of an extension wire.

Various types of guide wire extension systems are known in the art. Examples of extendible guide wires are disclosed in U.S. Pat. Nos. 4,827,941 to Taylor et al., 4,917,103 to Gambale et al., and 4,966,163 to Krause et al. These extension systems utilize mechanical couplings to connect the guide wire to the extension wire. There are several disadvantages associated with the use of mechanical couplings. For example, some mechanical couplings utilize material deformation or friction to make a secure connection. Such a design makes the mechanical coupling susceptible to damage and malfunction when the coupling is disconnected and subsequently reconnected. Other mechanical couplings such as threaded connections, require fine digital manipulations to secure the guide wire to the extension wire. These mechanical couplings are cumbersome unless the operator has sufficient experience in their use. Accordingly, there is a need for an extension system that avoids some of the disadvantages associated with mechanical couplings.

SUMMARY OF THE INVENTION

The present invention overcomes the disadvantages of the prior art and provides an extension system which is both durable and relatively easy to use.

The present invention may be described as a guide wire extension system including a guide wire and an extension wire and means for magnetically coupling the guide wire to the extension wire. The magnetic coupling means may include a magnetic portion and a magnetically-responsive portion. Alternatively, the magnetic coupling may include a first magnet portion and a second magnet portion. The magnetic coupling means may include a plurality of magnets aligned along a common axis.

The present invention may also be described as a method of extending the usable length of a guide wire, including the steps of providing a guide wire with a magnetic coupling, providing an extension wire with a magnetic coupling, and connecting the magnetic coupling of the guide wire to the magnetic coupling of the extension wire. The method of extending the usable length of the guide wire may also include the steps of disconnecting and reconnecting the magnetic couplings as may be required in a medical procedure.

DETAILED DESCRIPTION OF THE INVENTION

The following detailed description should be read with reference to the drawings in which similar parts in different drawings are numbered identically. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

Figure 1:
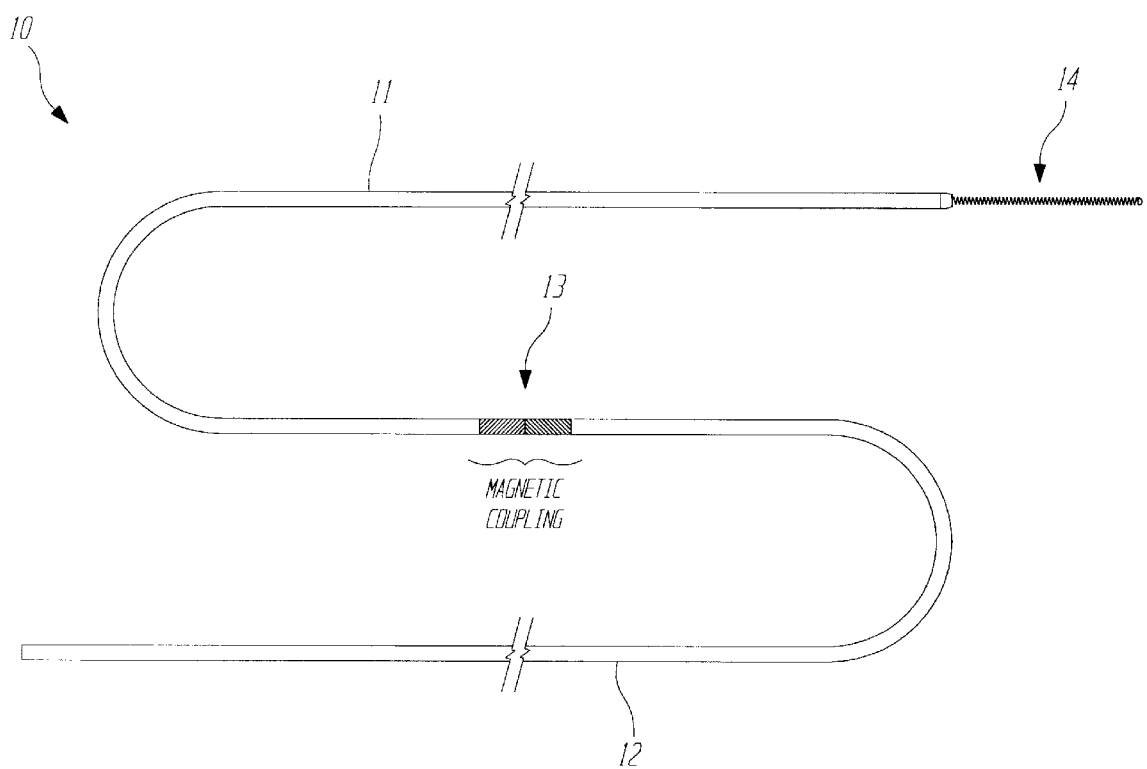
FIG. 1 illustrates a plan view of the guide wire extension system of the present invention.

Refer now to FIG. 1 which shows a plan view of the guide wire extension system 10 of the present invention. Guide wire extension system 10 includes a guide wire 11 which is releasably connectable to an extension wire 12 by magnetic coupling 13. Guide wire 11 may include a spring tip 14 to facilitate atraumatic navigation through the vascular system.

Magnetic coupling 13 produces an attractive force which has a sufficiently large longitudinal component to magnetically couple the guide wire 11 to the extension wire 12. The lateral component is sufficiently small to permit relative rotation between the guide wire 11 and the extension wire 12.

Empirical data demonstrates that about 50 grams of longitudinal force is required to reliably connect the guide wire 11 to the extension wire 12 while a conventional PTCA balloon catheter is being removed. Depending on the factor of safety desired, larger longitudinal forces (e.g., 100 grams) may be generated. Using the materials and dimensions described with reference to FIGS. 2–5, approximately 5 grams of longitudinal force may be generated per magnet/magnetically responsive section. Accordingly, the embodiments of FIGS. 2a and 2b employing about 10 magnet/magnetically responsive sections are preferred in order to generate 50 grams of longitudinal force. It is contemplated, however, that some medical procedures may not require 50 grams of longitudinal force and therefore the embodiments of FIGS. 3–5 would be satisfactory. Furthermore, it is contemplated that the materials described herein may be improved upon in order to generate larger magnetic forces. Improved material may generate more than 5 grams per magnet/magnetically responsive section and therefore the embodiments of FIGS. 3–5 would be satisfactory.

It is contemplated that guide wire 11 and extension wire 12 may be made of conventional materials and may have conventional dimensions. For example, guide wire 11 and extension wire 12 may be made of stainless steel each having a length of about 150 cm and a diameter ranging from 0.010 inches to about 0.025 inches.

Refer now to FIGS. 2–5 which show longitudinal cross-sectional views of various embodiments of the magnetic coupling 13 of the guide wire extension system 10. It is contemplated that each magnetic coupling illustrated in FIGS. 2–5 may be arranged as shown between the guide wire 11 and the extension wire 12. Alternatively, it is contemplated that each magnetic coupling illustrated in FIGS. 2–5 may be reversed such that the portion of the magnetic coupling rigidly connected to the guide wire 11 is rigidly connected to the extension wire 12 and vice versa. It is further contemplated that each magnetic coupling illustrated in FIGS. 2–4 may include a magnetic portion in place of the magnetically responsive portion.

Figure 2A:
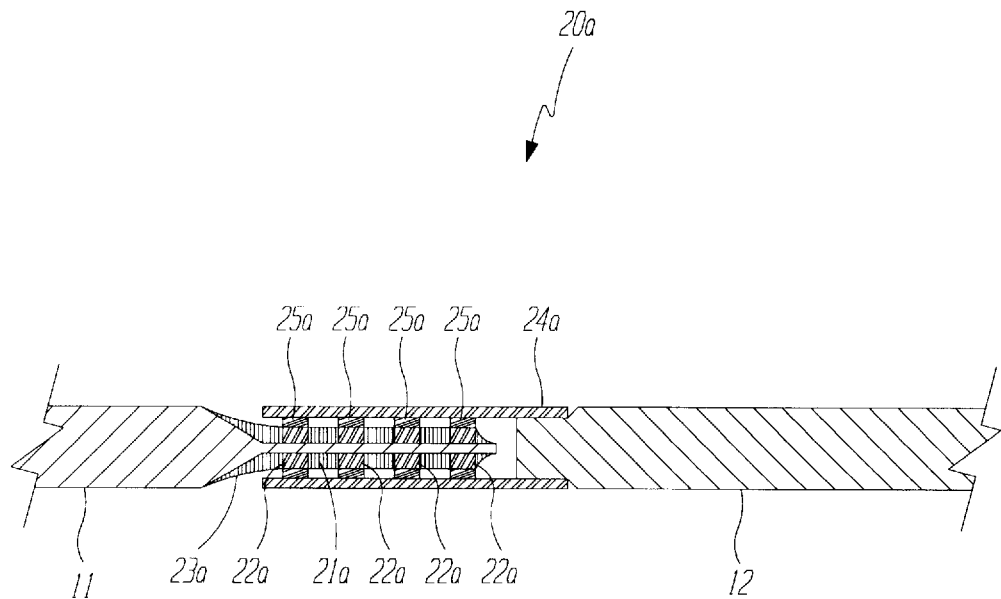
FIGS. 2–5 illustrate longitudinal cross-sectional views of various embodiments of the magnetic coupling of the present invention.

Refer now to FIG. 2a in which guide wire 11 is connected to extension wire 12 by articulated magnetic coupling 20a. Articulated magnetic coupling 20a includes a series of inner magnets 22a rigidly secured to core member 21a by filler material 23a. Filler material 23a is non-magnetic and non-magnetically responsive. Articulated magnetic coupling 20a further includes a series of magnetically responsive outer portions 25a which are rigidly connected to hypotube 24a which in turn is rigidly connected to extension wire 12. Inner magnets 22a are coaxially aligned with magnetically responsive outer portions 25a and are slidable therein. The arrangement of each magnetically responsive outer portion 25a relative to each inner magnet 22a is such that the interaction between them produces an optimal attractive force. Providing a series of inner magnets 22a and magnetically responsive outer portions 25a increases the quantity of magnetic field edge effects which contribute a substantial amount of the longitudinal force to resist relative longitudinal displacement. Accordingly, the number of inner magnets 22a and magnetically responsive outer portions 25a may be varied, depending on the amount of longitudinal force required or desired to couple the guide wire 11 to the extension wire 12.

Core member 21a may be formed by grinding or etching the proximal end of the guide wire 11 to a diameter of about 0.005 to 0.010 inches and a length of about 2 to 5 inches. Approximately 5 to 20 inner magnets may be symmetrically disposed on the core member 21a and secured in place utilizing a suitable filler material 23a such as a medical grade adhesive. The filler material 23a may partially fill the voids between each inner magnet 22a or filler material 23a may completely fill the voids (as shown) between each inner magnet 22a to produce a smooth and continuous outer surface. Inner magnets 22a may be made of Alnico available from Mag Star Technologies, Minneapolis, Minn. or neodymium boron iron having an inner diameter approximately equal to the diameter of the core member 21a, an outer diameter of about 0.008 to 0.012 inches and a length of about 0.10 to 0.40 inches. Each inner magnet 22a may be spaced approximately 0.10 to 0.40 inches apart, depending in part on the length of each individual inner magnet 22a. Magnetically responsive outer portions 25a may have an inner diameter slightly larger than the outer diameter of the inner magnets 22a, an outer diameter of approximately 0.010 to 0.014 inches and a length approximately equal to the length of the inner magnets 22a. Magnetically responsive outer portions 25a may be made of Hiperco Alloy 50 (available from Carpenter Steel in Reading, Pa.) and may be secured to hypotube 24a by utilizing a suitable medical grade adhesive such as epoxy or cyanoacrylate. Hypotube 24a may have an outer diameter approximately equal to the diameter of the extension wire, an inner diameter approximately equal to the outer diameter of the magnetically responsive outer portions 25a, and a length of approximately 2.5 to 5.5 inches. Hypotube 24a may be made of 304v stainless steel and may be secured to extension wire 12 utilizing a solder or weld joint.

Figure 2B:
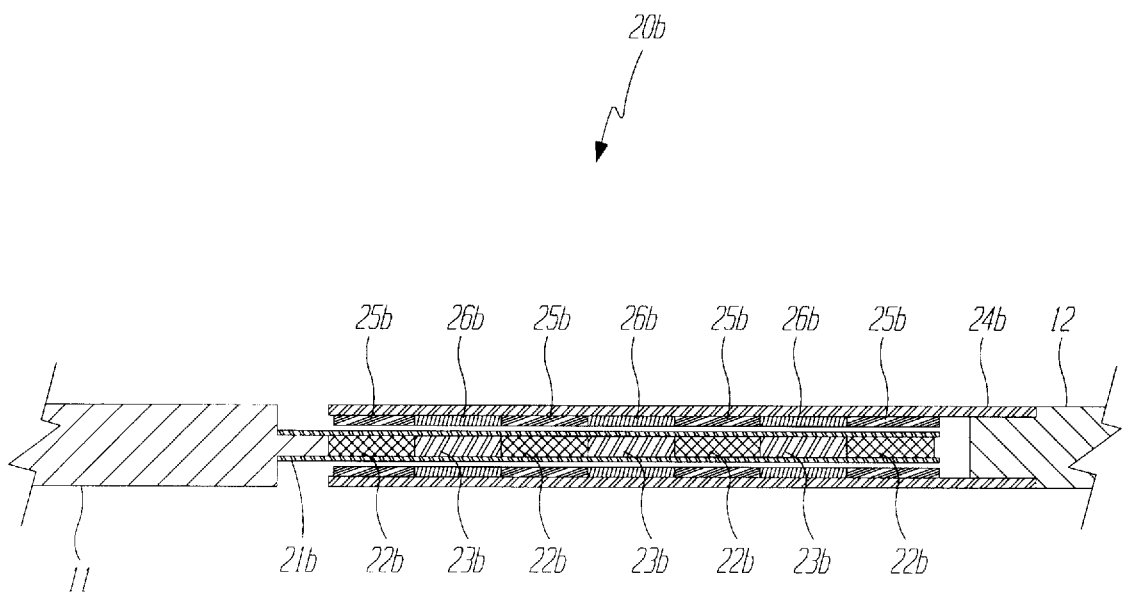

Refer now to FIG. 2b in which guide wire 11 is connected to extension wire 12 by an alternative articulated magnetic coupling 20b. Alternative articulated magnetic coupling 20b includes a series of inner magnets 22b rigidly secured inside core tube 21b. Filler material 23b is non-magnetic and non-magnetically responsive. Alternative articulated magnetic coupling 20b further includes a series of magnetically responsive outer portions 25b which are rigidly connected to outer tube 24b which in turn is rigidly connected to extension wire 12. Inner magnets 22b are coaxially aligned with magnetically responsive outer portions 25b and are sidable therein. The arrangement of each magnetically responsive outer portion 25b relative to each inner magnet 22b is such that the interaction between them produces an optimal attractive force. Providing a series of inner magnets 22b and magnetically responsive outer portions 25b increases the magnitude of magnetic field edge effects which contribute a substantial amount of the longitudinal force to resist relative longitudinal displacement. Accordingly, the number of inner magnets 22b and magnetically responsive outer portions 25b may be varied, depending on the amount of longitudinal force required or desired to couple the guide wire 11 to the extension wire 12.

Core tube 21b may be made of polyimide having an inside diameter of about 0.007 to 0.008 inches, an outside diameter of about 0.009 to 0.010 inches and a length of about 2 to 5 inches. Approximately 5 to 20 inner magnets may be symmetrically disposed in the core tube 21b and secured in place utilizing a suitable medical grade adhesive. Filler material 23b may be non-magnetic wire sections such as a nickel titanium alloy, non-magnetic stainless steel, or plastic rod. Inner magnets 22b may be made of Alnico available from Mag Star Technologies, Minneapolis, Minn. or neodymium boron iron having an outer diameter approximately equal to the inside diameter of the core tube 21b and a length of about 0.10 to 0.40 inches. Each inner magnet 22b may be spaced approximately 0.10 to 0.40 inches apart, depending in part on the length of each individual inner magnet 22b. Magnetically responsive outer portions 25b may have an inner diameter slightly larger than the outer diameter of the core tube 21b, an outer diameter of approximately 0.010 to 0.014 inches and a length approximately equal to the length of the inner magnets 22b. Magnetically responsive outer portions 25b may be made of Hiperco Alloy 50 and may be secured to outer tube 24b by utilizing a suitable adhesive such as epoxy or cyanoacrylate. Filler material 26b may be hypotube sections of any non-magnetic material, preferably a high tensile metal such as stainless steel alloys. Filler materials 23b and 26b are solid non-magnetic pieces in their final form to maintain exact spacing. Outer tube 24b may have an outer diameter approximately equal to the diameter of the extension wire, an inner diameter approximately equal to the outer diameter of the magnetically responsive outer portions 25b, and a length of approximately 2.5 to 5.5 inches. Outer tube 24b may be made of polyimide or stainless steel and may be secured to extension wire 12 using an appropriate connector such as a medical grade adhesive, solder, or weld.

It is contemplated that the magnetically responsive potions 25a and 25b may be an integral part of the guide wire 11 (or the extension wire 12). In particular, magnetically responsive potions 25a and 25b would be formed of the same material as the guide wire 11 (or extension wire 12) such as 400 series cold-drawn stainless steel. A bore hole with recesses may be plunge ground into the end of the guide wire 11, and the recesses may be back filled with a suitable non-magnetic material. The magnetic portions 22a and 22b would be formed as described previously.

Figure 3:
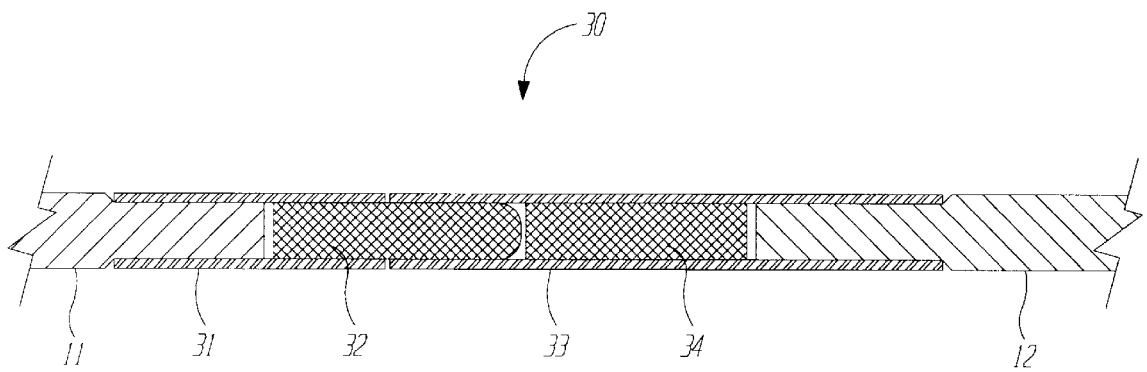

Refer now to FIG. 3 in which guide wire 11 is connected to extension wire 12 by end-to-end magnetic coupling 30. End-to-end magnetic coupling 30 includes magnet 32 which is rigidly connected to hypotube 31 which in turn is rigidly connected to guide wire 11. End-to-end magnetic coupling 30 further includes magnetically responsive portion 34 which is rigidly connected to hypotube 33 which in turn is rigidly connected to extension wire 12. Magnet 32 is coaxially aligned with hypotube 33 and is sidable therein. Accordingly, magnet 32 is aligned with magnetically responsive portion 34 in an end-to-end relationship when the magnet 32 is disposed in the hypotube 33. The arrangement of magnet 32 and magnetically responsive portion 34 is such that the interaction between them produces an optimal attractive force. This attractive force has a sufficient longitudinal component to magnetically couple the guide wire 11 to the extension wire 12.

Hypotube 31 may be made of a suitable medical grade metal such as 304v stainless steel having an outer diameter approximately equal to the diameter of the guide wire, a wall thickness of about 0.002 to 0.005 inches, and a length of about 0.5 to 1.5 inches. In a similar manner, hypotube 33 may be made of a suitable medical grade metal such as 304v stainless steel having an outer diameter approximately equal to the diameter of the extension wire, a wall thickness of about 0.002 to 0.005 inches, and a length of about 1.0 to 2.0 inches. Magnet 32 may be made of Alnico available from Mag Star Technologies, Minneapolis, Minn. or neodymium boron iron and magnetically responsive portion 34 may be made of Hiperco Alloy 50. Magnet 32 and magnetically responsive portion 34 may have an outer diameter of about 0.008 to 0.040 inches and a length of about 0.01 to 0.20 inches. The attractive force between magnet 32 and magnetically responsive portion 34 is proportional to their cross-sectional area. Accordingly, the attractive force may be considerable larger for larger diameter guide/extension wires. Magnet 32 may be secured to hypotube 31 and magnetically responsive portion 34 may be secured to hypotube 33 utilizing a suitable medical grade adhesive such as epoxy or cyanoacrylate. Hypotube 31 may be connected to guide wire 11, and hypotube 33 may be connected to extension wire 12 utilizing a conventional solder or weld joint.

Figure 4:
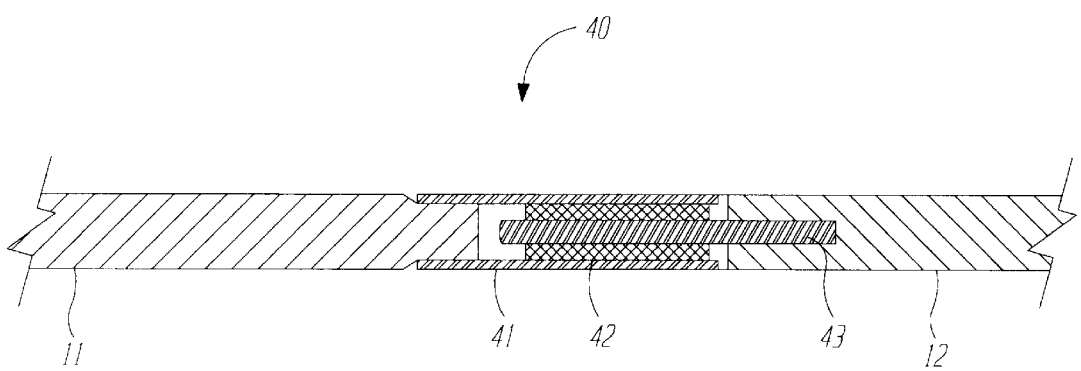

With reference to FIG. 4, guide wire 11 is connected to extension wire 12 by coaxial magnetic coupling 40. Coaxial magnetic coupling 40 includes magnetically responsive outer portion 42 which is rigidly connected to hypotube 41 which in turn is rigidly connected to guide wire 11. Coaxial magnetic coupling 40 further includes inner magnet 43 which is rigidly connected to extension wire 12. Inner magnet 43 is coaxially aligned with magnetically responsive outer portion 42 and is slidable therein. The arrangement of the magnetically responsive outer portion 42 relative to the inner magnet 43 is such that the interaction between them produces an optimal attractive force. This attractive force has a longitudinal component which resists relative longitudinal displacement. Accordingly, when inner magnet 43 is disposed in magnetically responsive outer portion 42, the guide wire 11 is magnetically coupled to the extension wire 12.

Hypotube 41 may be made of a suitable medical grade metal such as 304v stainless steel having an outer diameter approximately equal to the diameter of the guide wire, a wall thickness of about 0.002 to 0.005 inches, and a length of about 0.5 to 1.0 inches. Magnetically responsive outer portion 42 may be made of Hiperco Alloy 50 having an outer diameter approximately equal to the inner diameter of the hypotube 41, a wall thickness of about 0.002 to 0.004, and a length of about 0.10 to 0.50 inches. Magnetically responsive outer portion 42 may be secured to hypotube 41 with a suitable medical grade adhesive such as epoxy or cyanoacrylate. Hypotube 41 may be secured to guide wire 11 utilizing a solder or weld joint.

Inner magnet 43 may be made of Alnico available from Mag Star Technologies, Minneapolis, Minn. or neodymium boron iron having a diameter slightly less than the inner diameter of the magnetically responsive outer portion 42 and a length of about 0.10 to 0.50 inches. Preferably, the exposed end of inner magnet 43 is tapered or rounded to facilitate easy insertion into the magnetically responsive outer portion 42. Inner magnet 43 may be secured to extension wire 12 utilizing a suitable medical grade adhesive such as epoxy or cyanoacrylate.

Figure 5:
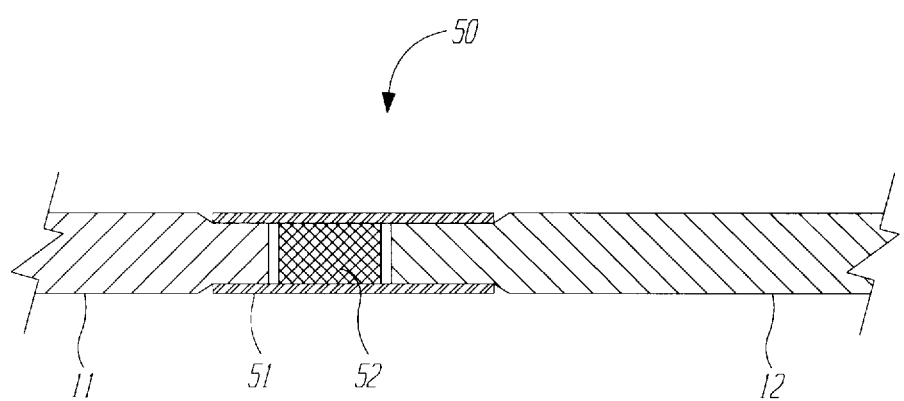

Refer now to FIG. 5 in which guide wire 11 is magnetically coupled to extension wire 12 by single magnet coupling 50. Single magnet coupling 50 utilizes an extension wire 12 that is magnetically responsive and attracted to magnet 52. Magnet 52 is rigidly connected to hypotube 51 which in turn is rigidly connected to guide wire 11. Alternatively, it is contemplated that guide wire 11 may be magnetically responsive with magnet 52 rigidly connected to extension wire 12. Magnetically responsive extension wire 12 is sufficiently magnetically attracted to magnet 52 to produce a longitudinal force which resists relative longitudinal displacement. Accordingly, when extension wire 12 is disposed in hypotube 51 adjacent magnet 52, the extension wire 12 is magnetically coupled to the guide wire 11.

In this embodiment, extension wire 12 must be made of a magnetically responsive material such as cold-drawn 400 series stainless steel. Magnet 52 may be made of Alnico available from Mag Star Technologies, Minneapolis, Minn. or neodymium boron iron having an outer diameter approximately equal to the inner diameter of the hypotube 51 and a length of about 0.10 to 0.50 inches. Hypotube 51 may be made of stainless steel having an outer diameter approximately equal to the diameter of the guide wire 11, a wall thickness of about 0.002 to 0.005 inches and a length of about 1.0 to 2.0 inches. Hypotube 51 may be secured to guide wire 11 by utilizing a conventional solder or weld joint. Magnet 52 may be secured to hypotube 51 utilizing a medical grade adhesive such as epoxy or cyanoacrylate.

It is contemplated that guide wire extension system 10 may be used in a substantially similar manner as other conventional extension systems with the exception of connecting and disconnecting magnetic coupling 13. As mentioned previously, magnetic coupling 13 produces sufficient longitudinal forces to resist longitudinal displacement of the guide wire 11 relative to the extension wire 12. This longitudinal force is sufficiently large to avoid inadvertent disconnection and sufficiently small to allow easy disconnection by the operator. Since magnetic coupling 13 is not a mechanical connection, repeated use will not reduce the integrity of the coupling. In addition, since magnetic coupling 13 is engaged and disengaged by simple linear motion, magnetic coupling 13 is very simple to use.

While the specification describes the preferred embodiments, those skilled in the art will appreciate the scope and spirit of the invention with reference to the appended claims.

What is claimed is:

1. A guide wire extension system, comprising:
   a. a guide wire having a proximal end;
   b. an extension wire having a distal end disposed adjacent the proximal end of the guide wire; and
   c. means for magnetically coupling the proximal end of the guide wire to the distal end of the extension wire in an end-to-end relationship, the magnetic coupling means including a receiving portion and an insertion portion wherein the insertion portion is adapted to be inserted into the receiving portion, the magnetic coupling means further including a magnet portion and a magnetically responsive portion, wherein the magnetic portion includes a plurality of magnets.

2. A guide wire extension system as in claim 1, wherein the magnetically responsive portion includes a plurality of magnetically responsive elements.

3. A guide wire extension system as in claim 2, wherein the plurality of magnets are aligned along a common axis.

4. A guide wire extension system as in claim 3, wherein the magnetically responsive elements are aligned along the common axis.

5. A guide wire extension system as in claim 4, wherein the magnetic portion is coaxially disposed in the magnetically responsive portion.

6. A guide wire extension system, comprising:
   a. a guide wire having a proximal end;
   b. an extension wire having a distal end disposed adjacent the proximal end of the guide wire; and
   c. a magnetic coupling connected to the proximal end of the guide wire and the distal end of the extension wire, the magnetic coupling including a receiving portion and an insertion portion wherein the insertion portion is adapted to be inserted into the receiving portion, the magnetic coupling further including a magnet portion and a magnetically responsive portion, wherein the magnetic portion includes a plurality of magnets.

7. A guide wire extension system as in claim 6, wherein the magnetically responsive portion includes a plurality of magnetically responsive elements.

8. A guide wire extension system as in claim 7, wherein the plurality of magnets are aligned along a common axis.

9. A guide wire extension system as in claim 8, wherein the plurality of magnetically responsive portions are aligned along the common axis.

10. A guide wire extension system as in claim 9, wherein the magnetic portion is coaxially disposed in the magnetically responsive portion.

11. A method of extending the effective length of a guide wire, comprising the steps of:
    i. providing a guide wire having a proximal end and a first portion of a magnetic coupling attached to the proximal end;
    ii. providing an extension wire having a distal end and a second portion of the magnetic coupling attached to the distal end; and
    iii. connecting the first portion of the magnetic coupling to the second portion of the magnetic coupling by inserting one of the first and second portions into the other of the first and second portions such that the guide wire and the extension wire are coaxially aligned in an end-to-end relationship.

12. A method of extending the usable length of a guide wire as in claim 11, further comprising the step of:
    iv. performing an operation with an intravascular device disposed on the guide wire.

13. A method of extending the usable length of a guide wire as in claim 12, further comprising the step of:
    v. disconnecting the first portion of the magnetic coupling from the second portion of the magnetic coupling.

14. A guide wire extension system as in claim 6, wherein the insertion portion is tapered.

15. A guide wire extension system as in claim 6, wherein the receiving portion and the insertion portion are coaxially aligned.

16. A guide wire extension system as in claim 6, wherein the receiving portion and the insertion portion are arranged end-to-end.

17. A guide wire extension system as in claim 6, wherein the receiving portion and the insertion portion are articulated.

* * * * *

UNITED STATES PATENT AND TRADEMARK OFFICE
CERTIFICATE OF CORRECTION

PATENT NO. : 5,813,996

DATED : September 29, 1998

INVENTOR(S) : ST. GERMAIN et al.

It is certified that error appears in the above-identified patent and that said Letters Patent is hereby corrected as shown below:

At column 4, line 26, "sidable" should be --slidable--.

At column 5, line 25, "sidable" should be --slidable--.

Signed and Sealed this

Twelfth Day of January, 1999

*Attest:*

*Attesting Officer*    *Acting Commissioner of Patents and Trademarks*